(12) United States Patent
Smythe

(10) Patent No.: US 6,702,745 B1
(45) Date of Patent: Mar. 9, 2004

(54) 3D/4D ULTRASOUND IMAGING SYSTEM

(76) Inventor: David Smythe, 191 Wilton Street, Glasgow G20 6DF (GB)

( * ) Notice: Subject to any disclaimer, the term of this patent is extended or adjusted under 35 U.S.C. 154(b) by 0 days.

(21) Appl. No.: 09/889,781

(22) PCT Filed: Jan. 21, 2000

(86) PCT No.: PCT/GB00/00167
§ 371 (c)(1),
(2), (4) Date: Oct. 17, 2001

(87) PCT Pub. No.: WO00/43809
PCT Pub. Date: Jul. 27, 2000

(30) Foreign Application Priority Data

Jan. 21, 1999 (GB) .............................. 9901306

(51) Int. Cl.[7] ................................ A61B 8/00
(52) U.S. Cl. ................................ 600/443
(58) Field of Search ............... 600/437, 443, 600/447; 128/916, 922; 73/602

(56) References Cited

U.S. PATENT DOCUMENTS

| | | | |
|---|---|---|---|
| 4,387,697 A | 6/1983 | Duke ........................ 124/89 |
| 4,435,984 A | 3/1984 | Gruber ...................... 73/628 |
| 4,456,982 A | 6/1984 | Tournois .................... 367/11 |
| 4,598,366 A | * 7/1986 | Devaney ..................... 73/602 |
| 4,604,697 A | * 8/1986 | Luthra et al. ................ 73/602 |
| 4,944,036 A | 7/1990 | Hyatt ........................ 367/43 |
| 5,079,749 A | * 1/1992 | Aminzadeh et al. .......... 367/73 |
| 5,103,427 A | * 4/1992 | Erdol et al. .................. 367/7 |
| 5,269,309 A | * 12/1993 | Fort et al. ................... 73/597 |
| 5,628,320 A | * 5/1997 | Teo .......................... 128/916 |
| 5,673,697 A | * 10/1997 | Bryan et al. ............... 128/916 |
| 5,871,446 A | 2/1999 | Wilk ......................... 600/407 |
| 5,966,169 A | 10/1999 | Bullis ........................ 348/81 |
| 6,005,916 A | * 12/1999 | Johnson et al. ............. 600/425 |
| 6,135,960 A | * 10/2000 | Holmberg ................... 600/447 |

FOREIGN PATENT DOCUMENTS

GB 1446022 8/1976

* cited by examiner

Primary Examiner—Francis J. Jaworski
(74) Attorney, Agent, or Firm—Fleshner & Kim, LLP

(57) ABSTRACT

Method and apparatus for 3D/4D ultrasonic imaging. An array of ultrasonic sources and receivers (7) positioned over or near tissue (6) transmit short encoded omnidirectional ultrasonic shots (9). The amplitude and phase of the resulting reflected waves (10) are detected, sampled and digitised. Traces from each shot are reconstructed by digital data processing. A three dimensional data volume is constructed corresponding to reflection amplitude through a regular volume. The data volume may then be imaged through any arbitrary plane. Time varying images can be readily produced as the process takes only a fraction of a second.

30 Claims, 2 Drawing Sheets

3D/4D ULTRASOUND IMAGING SYSTEM

Ultrasound imaging is commonly used for medical diagnostics as it represents a safe and non-invasive technique for real-time imaging. The most commonly used devices at the present time produce 2D images of planes through imaged tissue.

Typically, these images are produced using one or two dimensional arrays of ultrasound sources/receivers which transmit/receive highly directional, short, radio-frequency (typically 3–20 MHz) pulses, with a bandwidth of under one octave.

Individual scans may be one-dimensional (wavefront axial or paraxial) or two-dimensional (wavefield confined to a plane) and use arrays of sources and receivers which are distributed along a line or around a circle. In each case, energy is commonly focussed to target depths within the tissue and the amplitude of reflected energy is detected and used to form the image. Ultrasonic waves may be scattered and modified by a variety of physical processes; however, the term "reflected" will be used herein to refer to all ultrasonic waves including all forms of elastic waves reaching the receivers due originally to the ultrasonic sources. Furthermore, the terms "ultrasound" and "ultrasonic" will be used in a more general form than usual herein, to include all forms of high frequency elastic waves, and not just acoustic (sonic, or sound) waves.

Medical practitioners typically wish to study three dimensional structures. A three dimensional effect can be imitated by moving a 2D-ultrasound scanner around interactively and examining continually updated 2D-images. This is unsatisfactory in practice as it is slow compared with the motion of tissue, particularly motion related to the cycle of heart beat and blood flow. Furthermore, the directionality and focussing depth of the 2D images are commonly fixed, often leaving gaps in the reflectivity information.

It would therefore be desirable to provide a 3D imaging system which used true 3D geometry, rather than simply combining information from individual 2D slices. In particular, it would be advantageous to be able to collect and process data for a 3D volume holistically, rather than focussing solely on individual features within the body.

Some 3D imaging systems have been devised which operate by performing a series of 2D scans to provide a 3D record of tissue. These provide additional information to the user; however, image production is slow compared with periodic movements in tissue and typically require several seconds to several minutes to provide images. It would clearly be advantageous to provide an imaging system capable of providing a complete picture in less than the duration of a single human heart beat (say, 1 second).

Furthermore, medical practitioners also wish to view time-varying ultrasound images and, indeed, conventional 2D ultrasound imagers will typically display a rapidly updated image. However, the 3D scanning techniques which compose their image from multiple 2D scans are unsatisfactory for this purpose due to the length of time required. Partly, they are unsatisfactory to watch as the update time is long. In particular, as the update time is long relative to the timescale of periodic tissue movements, accurate time-varying imaging requires use of complex additional techniques such as attempting to strobe the images in phase with the repetitive cyclic motion.

It would therefore be advantageous to provide a system capable of producing time-varying 3D images (4D-images) with an update time faster than the duration of a single heartbeat, preferably much faster.

The following referenced documents, discussed below, contain prior art in the fields of geophysics and pre-stack migration and their disclosure is incorporated herein by reference:

1. Geyer, R. L. (editor), 1989. *Vibroseis.* Geophysical Reprint Series Number 11. Society of Exploration Geophysicists, Tulsa, Okla., 830 pp.
2. Yilmaz, O., 1987. Seismic Data Processing. *Investigations in Geophysics*, Volume 2, Society of Exploration Geophysicists, Tulsa, Okla., 526 pp.
3. *Geophysics*, volumes 1–64, 1936–1999, Society of Exploration Geophysicists, Tulsa, Okla.
4. *The Leading Edge* (Full title: *Geophysics, The Leading Edge of Exploration*), volumes 1–18, 1982–1999, Society of Exploration Geophysicists, Tulsa, Okla.
5. *Geophysical Prospecting*, volumes 1–47, 1953–1999, European Association of Geoscientists and Engineers (formerly European Association of Exploration Geophysicists), Houten, The Netherlands.
6. *First Break*, volumes 1–17, 1983–1999, European Association of Geoscientists and Engineers (formerly European Association of Exploration Geophysicists), Houten, The Netherlands.
7. Bancroft, J. C., 1997. *A practical Understanding of Pre- and Poststack Migrations.* Volume 1 (Poststack). Course Notes Series Number 7, Society of Exploration Geophysicists, Tulsa, Okla.

Bancroft, J. C., 1998. *A practical Understanding of Pre- and Poststack Migrations.* Volume 2 (Prestack). Course Notes Series Number 9, Society of Exploration Geophysicists, Tulsa, Okla.

SUMMARY OF THE INVENTION

According to a first aspect of the present invention there is provided a method for elastic wave imaging of a three dimensional object using an array of elastic wave sources and receivers of known position, the method comprising the steps of:

(a) the elastic wave sources emitting elastic wave pulses that are reflected within the volume of the three dimensional object;

(b) the elastic wave receivers measuring the reflected elastic wave pulses;

(c) constructing an image of the three dimensional object from the resulting record of the reflected elastic wave pulses.

characterized in that the elastic wave pulses are ultrasound pulses, the elastic wave sources are ultrasound sources, the elastic wave receivers are ultrasound receivers, the ultrasound receivers measure both the phase and amplitude of the ultrasound pulses, that both phase and amplitude information of the reflected ultrasound pulses is retained and used in constructing an image of the three dimensional object.

An ultrasound pulse may comprise a shot, a shot being a discrete emission of ultrasound from a single ultrasound source.

Preferably, a shot is omnidirectional and point-like in character.

An ultrasound pulse may comprise a plurality of shots activated concurrently with appropriate time delays to produce an approximately planar wavefront moving in a prescribed direction.

Ultrasound pulses may be S-waves.

Typically, each ultrasound receiver records displacement, velocity or acceleration variation as a vector quantity.

Preferably, a plurality of traces are constructed and then used, in an otherwise known method, to construct an image of the three dimensional object, each trace being a record of the data recorded by an individual ultrasound receiver due to an individual ultrasound pulse.

Preferably, an ultrasound pulse is a known encoded signal defined by a time series.

More preferably, different elastic wave pulses are different known encoded signals.

Most preferably, the method includes the step of converting the traces to the form they would have had were each elastic wave pulse in the form of a sharp, short-duration pulse.

Optionally, only low-frequency data might be used for forming an image of the three dimensional object by using a truncated pilot sweep.

An individual ultrasound transducer may act as both an ultrasound source and an ultrasound receiver.

Typically, the position of the sources and receivers is known through their being incorporated onto a fixed, resilient recording surface.

The position and orientation of the recording surface may be monitored throughout data acquisition.

The recording surface may have apertures therein.

The ultrasound sources and ultrasound receivers may be positioned in a regular array.

An array of elastic wave sources and receivers may be separated from the three dimensional object by an ultrasound transmitting medium.

The ultrasound transmitting medium may be a fluid.

Some receivers may be linked together in parallel during data acquisition to form a receiver array.

Preferably, images are calculated in rapid succession to provide a time-varying three-dimensional record.

According to a second aspect of the present invention there is provided elastic wave imaging apparatus for producing an image of a three dimensional object, the apparatus comprising an array of elastic wave sources adapted to emit elastic wave pulses which are reflected within the volume of the three dimensional object, an array of elastic wave receivers for measuring the reflected elastic wave pulses, a dataprocessing means for calculating an image of the three dimensional object; characterized in that the elastic wave pulses are ultrasound pulses, the elastic wave sources are ultrasound sources, the elastic wave receivers are ultrasound receivers, the ultrasound receivers measure both the phase and amplitude of the ultrasound pulses, that both phase and amplitude information of the reflected ultrasound pulses is retained and used in constructing an image of the three dimensional object.

Typically, an ultrasound pulse comprises a shot, a shot being a discrete emission of ultrasound from a single ultrasound source.

Preferably, a shot is omnidirectional and point-like in character.

An ultrasound pulse may comprise a plurality of shots activated concurrently with appropriate time delays to produce an approximately planar wavefront moving in a prescribed direction.

Ultrasound pulses may be S-waves.

Preferably, each ultrasound receiver records displacement, velocity or acceleration variation as a vector quantity.

Preferably, a plurality of traces are constructed and then used, in an otherwise known method, to construct an image of the three dimensional object, each trace being a record of the data recorded by an individual ultrasound receiver due to an individual ultrasound pulse.

Preferably, an ultrasound pulse is a known encoded signal defined by a time series.

More preferably, different elastic wave pulses are different known encoded signals.

Preferably also, traces are converted to the form they would have had were each elastic wave pulse in the form of a sharp, short-duration pulse.

Optionally, only low-frequency data may be used for forming an image of the three dimensional object by using a truncated pilot sweep.

An individual ultrasound transducer may act as both an ultrasound source and an ultrasound receiver.

The position of the sources and receivers may be known through their being incorporated onto a fixed, resilient recording surface.

The position and orientation of the recording surface may be monitored throughout data acquisition.

The recording surface may have apertures therein.

Typically, the ultrasound sources and ultrasound receivers are positioned in a regular array.

Optionally, an array of elastic wave sources and receivers is separated from the three dimensional object by an ultrasound transmitting medium.

The ultrasound transmitting medium may be a fluid.

Some receivers may be linked together in parallel during data acquisition to form a receiver array.

Preferably, images are calculated in rapid succession to provide a time-varying three-dimensional record.

BRIEF DESCRIPTION OF THE DRAWINGS

An example embodiment of the present invention is described with reference to the following Figures.

DETAILED DESCRIPTION OF PREFERRED EMBODIMENTS

Figure 1A:
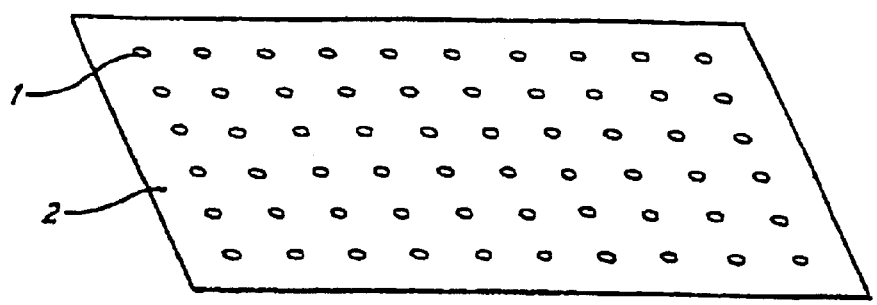
FIG. 1 shows perspective views of example shapes of the recording surface.
Figure 1B:
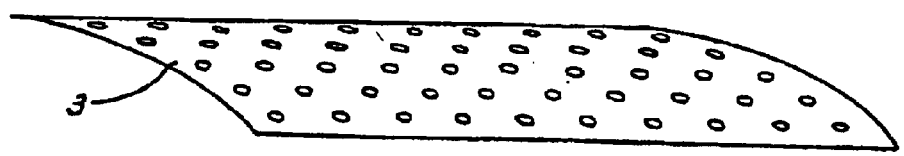
Figure 1C:
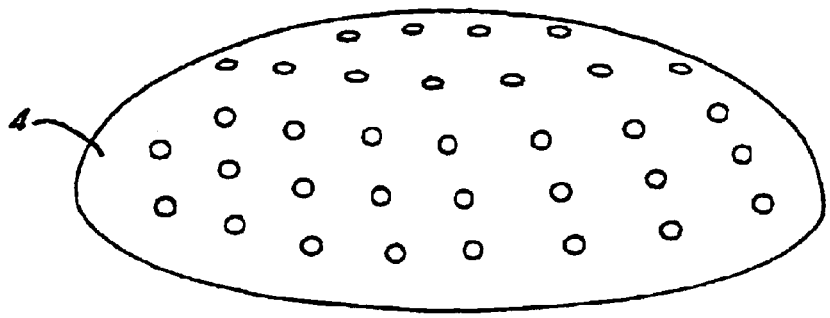

FIG. 1 shows example shapes of the recording surface. A plurality of piezo-electric ultrasonic combination source-receivers 1 is held in a fixed, known grid pattern. In the example embodiments, this surface may be planar 2, a segment of a cylinder 3 or a segment of a sphere 4. The recording surface may, however, be of arbitrary shape and dimension. The recording surface need not remain in one place throughout use and might be interactively moved by the user. The position and orientation of the recording surface is monitored throughout acquisition by standard methods.

The recording surface need not have an even distribution of sources and receivers. As an example, the surface may have a plurality of holes through it to permit instruments such as endoscopes and laparoscopes to be used. Therefore the volume of tissue may be imaged interactively during medical intervention procedures, and not merely as a diagnostic tool prior to medical intervention.

Figure 2:
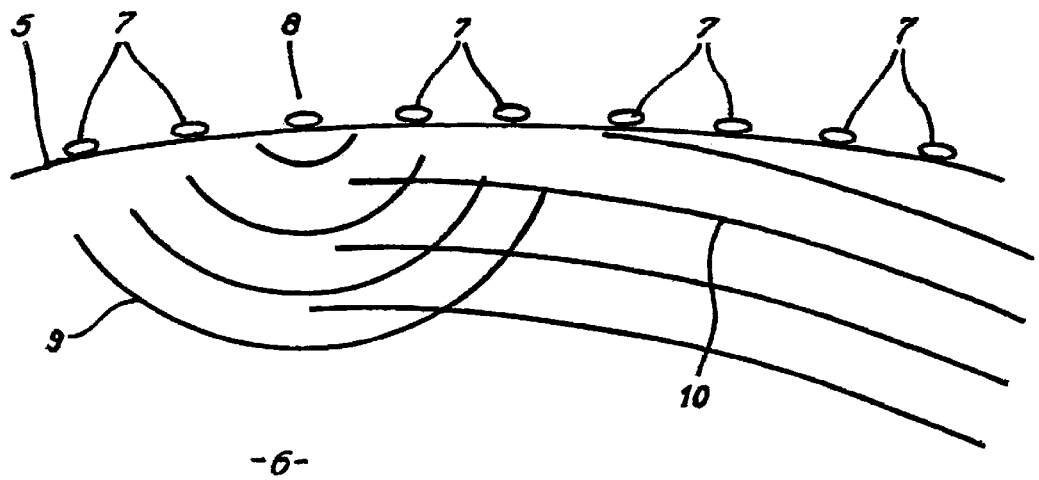
FIG. 2 shows a cross-section through an example recording surface positioned over tissue.

FIG. 2 shows a cross-section through an example embodiment of the recording surface 5 positioned over tissue 6. On the recording surface are fixed combination source/receivers 7. Each source is activated in turn 8 and transmits a short ultrasonic pulse referred to as a shot. The emitted ultrasonic pulse has at least one octave bandwidth (preferably more than three octaves) and transmits an approximately hemispherical wavefront 9 into this tissue. Preferably there should be little or no amplitude variation of the elastic energy distributed over the wavefront; that is to say, the source is omni-directional and point-like in character. Ultrasonic waves are reflected from structures in tissue and the reflected waves 10 are detected by receivers which record pressure information that is sampled and digitised in real time. Typically, a 16 bit word will be stored for each instantaneous pressure value. The resulting time series is referred to as a trace.

Each source may create an ultrasonic pulse comprising longitudinal or compressional waves, referred to as P-waves, or alternatively may produce an ultrasonic pulse comprising transversal or shear waves, referred to as S-waves.

Figure 3:
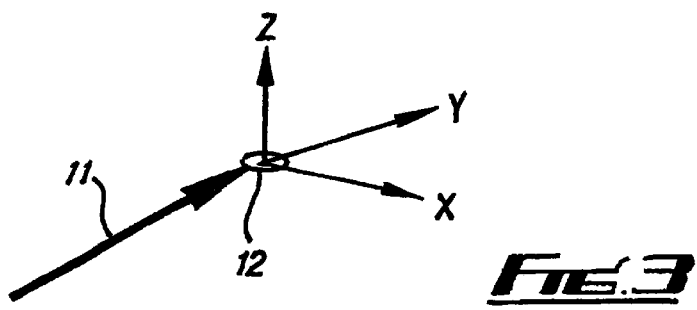
FIG. 3 shows a perspective view of orthogonal components of reflected shot energy expressed as a vector quantity.

Each receiver may detect the amplitude of the reflected energy as a displacement, as a velocity, or as an acceleration, and may transform the energy into an electrical signal. Each receiver may be capable of recording pressure variation with time as a scalar quantity resulting from the reflected shot energy. In an alternative embodiment each receiver may be capable of receiving the reflected shot energy as a vector quantity. In one example embodiment, each receiver may record the reflected energy in the form of three orthogonal components of the vector, resulting in three separate data traces for each receiver for each shot FIG. 3 shows a perspective view of such an embodiment, in which the three components labelled x, y and z are mutually perpendicular. The normal to the wavefront 11 strikes the receiver 12 which is designed such that the three components labelled x, y and z are recorded on separate channels (data streams). This method is especially advantageous since it facilitates the separation of reflected P-waves and S-waves, and additionally facilitates the recognition of other modes of elastic wave propagation such as surface waves.

Figure 4:
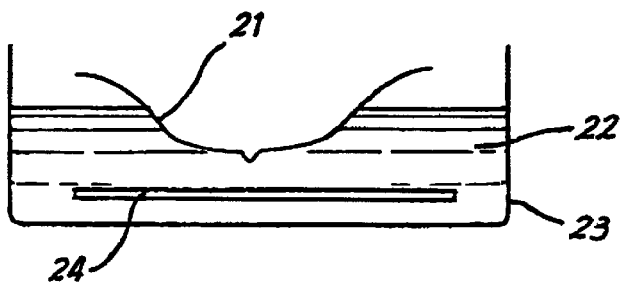
FIG. 4 shows a cross-section through an embodiment in which tissue immersed in liquid is imaged.

The recording surface need not necessarily be in direct physical contact with the tissue to be imaged, but may be separated from it by a fluid or solid medium having suitable elastic properties. FIG. 4 shows a cross-section through one example embodiment of such indirect contact, in which breast tissue 21 is immersed in a suitable liquid 22 contained within a container 23. The recording surface 24 lies below the tissue. This method is particularly advantageous as it involves negligible pressure distortion of the tissue, in contrast to existing ultrasound methods.

In the preferred embodiment, each shot is encoded; for example, each shot may consist of a chirp signal (a sweep) which rises from 100 to 1000 KHz over 1 ms. Such a sweep in which the frequency increases monotonically is defined as an upsweep. A sweep in which the frequency decreases monotonically is defined as a downsweep. Individual traces are then converted to the form which they would have had were each shot in the form of a sharp, short-duration pulse by application of standard data processing and compressing techniques including cross-correlating the individual traces with a recorded copy of the transmitted encoded signal. This copy is defined as the pilot sweep.

In an alternative embodiment, successive shots are encoded differently and the traces due to each are cross-correlated with the different appropriate shot signals. An important benefit of this technique is that, since the data resulting from successive shots can be distinguished after application of standard data processing techniques, it is not necessary for each shot to have died away to negligible levels before beginning the next shot This would speed up data collection which is highly advantageous for imaging rapidly moving objects. In one example embodiment, an upsweep and a downsweep may be initiated simultaneously from separate sources, but the reflected data from each source can be distinguished after cross-correlation of each trace with the appropriate pilot sweep, to yield two sets of data traces as if each shot had been initiated and recorded separately. The standard data acquisition and data processing techniques which are used in the field of geophysics and which use sweeps as a source signal are referred to collectively as the vibroseis technique (see for example, published reference 1). These techniques may be applied with appropriate spatial and temporal scaling to the area of medical ultrasound.

Once traces have been converted to the form which they would have were each shot in the form of a sharp, short-duration pulse they are used to form a three dimensional image by adaptation of techniques known in digital data processing in general and geophysical imaging in particular, as described, for example in published references 1–6. There are two principal approaches used to convert the traces into an image. The process may be described as migration. The first such approach performs the migration process after a plurality of traces has been summed or stacked, and may be referred to as post-stack migration (published reference 7 describes post-stack migration). It is summarised below by way of example:

Static corrections are applied to traces. That is to say, they are adjusted to earlier or later relative times to compensate for the non-planarity of the recording surface in most embodiments and any other delaying effects local to individual transmitters and receivers. Data are reduced to the form they would have if the recording surface had been a plane.

A common mid-point gather is used to form a first approximation to the reflection points within tissue.

The velocity of the elastic wave at each point within the volume of tissue to be imaged is determined using statistical methods such as semblance. As a first approximation, a constant velocity throughout the volume is assumed for the purpose of correcting the common-mid-point gather travel times using dip move-out.

Normal-move-out corrections are applied to each trace to correct for the different travel times due to different raypath lengths which have been traversed. It might be assumed that velocities are constant.

The many traces in each common-mid-point gather can now be summed to produce one output trace for each gather. This process, known as stacking, substantially reduces the volume of data whilst increasing the signal to noise ratio.

The imaging process, migration, is applied to the stacked traces as a post-stack process and moves the amplitude and phase information within each trace to the correct position corresponding to the location of each reflector or scatterer. Migration will be applied in 3-D and not confined to any 2-D slice.

In the second approach to imaging, the migration process may also be applied to data before stacking, and the approach may be called pre-stack migration (published reference 8 describes pre-stack migration); however, it is more processor-intensive than performing this operation on previously stacked data, but it is advantageous in that the resulting image may be more accurate.

Notwithstanding the approach employed, the output from this migration process is a 3D-data volume with digital records corresponding to reflection amplitude over a regular volume. The data volume might then be imaged through any arbitrary plane.

Note that as phase and amplitude have been preserved at every stage, trace attributes such as instantaneous frequency, phase and amplitude can be estimated via calculation of the complex trace from a single data trace.

Data from successive shots are grouped together to make the 3D image. The shooting process can be continuous so that a later group of shots can be used to make another 3D image at. a later time. A 4D time series of 3D images can therefore be produced.

Multiple reflections from any given reflector might be suppressed. Elastic waves other than compressional body waves or P-waves that are generated in solid tissue at the source or by mode conversion may be retained or suppressed.

The image may be constructed using only P-waves, or alternatively only S-waves. The use of S-waves may be particularly advantageous in medical ultrasound imaging in that S-wave images may be constructed in the presence of gaseous zones, for example within abdominal tissue, under conditions in which a P-wave image would be of relatively poor quality.

By way of illustration only, typical scales and parameters are listed below Many of these values could readily vary by an order of magnitude or more.

Taking the speed of sound in water as 1.5 km s$^{-1}$, and considering an encoded chirp signal rising from 100 to 1000 KHz in 0.1 ms gives ultrasound wavelengths from 15 to 1.5 mm and a width of the principal zero-lag peak of the Klauder wavelet of the order of 3 mm. Interpretative resolution of the resulting 3D volume, given that amplitude and phase information have been retained, is empirically one twentieth of this value, i.e. 0.15 mm.

It should be noted the resolution achieved in this example embodiment is equal to or better than that of conventional 2D systems, despite the fact that the source frequencies postulated are one to two orders of magnitude less than those used in conventional systems.

The aperture might consist of 50×50 active receivers spaced on a 2 mm square planar grid. The total area of this aperture is about 100 mm×100 mm and therefore suitable for depth penetration to around 100 mm. Sampling frequency would typically be 5 MHz (period 0.2 $\mu$s) giving a total data rate of 12.5 GHz. The length of each trace before correlation would be 1.2 ms (6000 samples) or 0.2 ms (1000 samples) after correlation. If a 16 bit word is used to store each reading, one shot comprises 30 Mb (uncorrelated) or 5 Mb (correlated) of data.

Typically, 100 consecutive shots are taken over 120 ms for each 3D stacked data volume. This is 250,000 traces. There will be 100×100=10,000 common-mid-point gathers at 1 mm spacing provided that the aperture has not been moved. The multiplicity of data (the fold) within each gather is therefore 25. This would provide a 3D data volume with an x-y spacing of 1 mm across a 100 mm×100 mm area with vertical resolution of 0.15 mm to a depth of 100 mm acquired in only 120 ms. The data have a bandwidth over three octaves and a dynamic range in amplitude of the order of 96 dB.

If, in the example illustration given above, it is required to produced a real-time 4D image of very rapidly moving tissue, the following adjustments may be made to the processing and imaging stages, but with a corresponding loss of resolution:

Only the lower-frequency data are used, by correlating the raw data traces with a pilot sweep which has been appropriately truncated.

The fold of coverage is reduced.

However, notwithstanding the above requirement for a real-time 4D image, the complete high-resolution dataset may simultaneously be recorded and processed without any loss of quality, for subsequent off-line viewing as an animated 4-D image.

The above embodiment is described for tissue imaging but could readily be adapted to imaging other materials. Such alternative embodiments include by way of example:

Imaging of animal tissue for veterinary purposes.

Imaging of dead human or animal tissue or tissue in vitro for forensic purposes.

Imaging of inanimate material to detect interior flaws in construction.

Further modifications and improvements may be incorporated without departing from the scope of the invention herein described.

What is claimed is:

1. A method for elastic wave imaging of a three dimensional object using an array of elastic wave sources and receivers of known position, the method comprising:

(a) the elastic wave sources emitting elastic wave pulses that are reflected within the volume of the three dimensional object;

(b) the elastic wave receivers measuring the reflected elastic wave pulses; and (c) constructing an image of the three dimensional object from the resulting record of the reflected elastic wave pulses, wherein the elastic wave pulses are ultrasound pulses, said pulses comprising known encoded signals of at least one octave in bandwidth, the elastic wave sources are ultrasound omnidirectional point-like sources, the elastic wave receivers are ultrasound receivers, the ultrasound receivers are configured to measure both the phase and amplitude of the ultrasound pulses, such that both phase and amplitude information of the reflected ultrasound pulses is retained and used in constructing an image of the three dimensional object.

2. The method for elastic wave imaging as claimed in claim 1, wherein an ultrasound pulse comprises a shot, and wherein a shot comprises a discrete emission of ultrasound from a single ultrasound source.

3. The method for elastic wave imaging as claimed in claim 2, wherein an ultrasound pulse comprises a plurality of shots activated concurrently with appropriate time delays to produce an approximately planar wavefront moving in a prescribed direction.

4. The method for elastic wave imaging as claimed in claim 1, wherein the ultrasound pulses are S-waves.

5. The method for elastic wave imaging as claimed in claim 1, wherein each ultrasound receiver is configured to record displacement, velocity or acceleration variation as a vector quantity.

6. The method for elastic wave imaging as claimed in claim 1, wherein a plurality of traces are constructed and then used, to construct an image of the three dimensional object, each trace comprising a record of the data recorded by an individual ultrasound receiver due to an individual ultrasound pulse.

7. The method for elastic wave imaging of claim 1, wherein different elastic wave pulses are different known encoded signals.

8. The method for elastic wave imaging as claimed in claim 1, further comprising converting the traces to a form they would have had were each elastic wave pulse in the form of a sharp, short-duration pulse.

9. The method for elastic wave imaging as claimed in claim 1, wherein only low-frequency data are used for forming an image of the three dimensional object by using a truncated pilot sweep.

10. The method for elastic wave imaging as claimed in claim 1, wherein a plurality of receivers are linked together in parallel during data acquisition to form a receiver array.

11. The method for elastic wave imaging as claimed in claim 1, wherein images are calculated in rapid succession to provide a time-varying three-dimensional record.

12. The method for elastic wave imaging as claimed in claim 1, wherein said pulses comprise known encoded signals of at least three octaves in bandwidth.

13. The method for elastic wave imaging as claimed in claim 1, wherein the ultrasound receivers are configured to measure the reflected ultrasound pulses simultaneously.

14. A method for elastic wave imaging as claimed in claim 1, wherein the measurements of phase and amplitude parameters from the ultrasound receivers are sampled, digitized, and stored in a plurality of time series and wherein said time series are used in constructing an image of the three dimensional object.

15. The method for elastic wave imaging of claim 14, further comprising converting the plurality of time series into an image by post-stack migration.

16. The method for elastic wave imaging as claimed in claim 14, further comprising the plurality of time series into an image by pre-stack migration.

17. The method for elastic wave imaging as claimed in claim 14, further comprising the complex trace from a single time series.

18. The method for elastic wave imaging as claimed in claim 17, further comprising estimating the instantaneous frequency, phase or amplitude from the complex trace.

19. An elastic wave imaging apparatus for producing an image of a three dimensional object, the apparatus comprising:

an array of elastic wave sources configured to emit elastic wave pulses which are reflected within the volume of the three dimensional object;

an array of elastic wave receivers configured to measure the reflected elastic wave pulses; and a data processor configured to calculate an image of the three dimensional object, wherein the elastic wave pulses are ultrasound pulses, said pulses comprising known encoded signals of at least one octave in bandwidth, the elastic wave sources are ultrasound omnidirectional point-like sources, the elastic wave receivers are ultrasound receivers, the ultrasound receivers are configured to measure both the phase and amplitude of the ultrasound pulses, that both phase and amplitude information of the reflected ultrasound pulses is retained and used in constructing an image of the three dimensional object.

20. The elastic wave imaging apparatus as claimed in claim 19, wherein an ultrasound pulse comprises a shot, and wherein a shot comprises a discrete emission of ultrasound from a single ultrasound source.

21. The elastic wave imaging apparatus as claimed in claim 20, wherein an ultrasound pulse comprises a plurality of shots activated concurrently with appropriate time delays to produce an approximately planar wavefront moving in a prescribed direction.

22. The elastic wave imaging apparatus as claimed in claim 19, wherein the ultrasound pulses are S-waves.

23. The elastic wave imaging apparatus as claimed in claim 19, wherein each ultrasound receiver is configured to record displacement, velocity or acceleration variation as a vector quantity.

24. The elastic wave imaging apparatus as claimed in claim 19, wherein a plurality of traces are constructed and then used, to construct an image of the three dimensional object, each trace comprising a record of the data recorded by an individual ultrasound receiver due to an individual ultrasound pulse.

25. The elastic wave imaging apparatus as claimed in claim 24, further comprising converting the traces to the form they would have had were each elastic wave pulse in the form of a sharp, short-duration pulse.

26. The elastic wave imaging apparatus as claimed in claim 19, wherein different elastic wave pulses are different known encoded signals.

27. The elastic wave imaging apparatus as claimed in claim 19, wherein only low-frequency data is used for forming an image of the three dimensional object by using a truncated pilot sweep.

28. The elastic wave imaging apparatus as claimed in claim 19, wherein an individual ultrasound transducer acts as both an ultrasound source and an ultrasound receiver.

29. The elastic wave imaging apparatus as claimed in claim 19, wherein a plurality of receivers are linked together in parallel during data acquisition to form a receiver array.

30. The elastic wave imaging apparatus as claimed in claim 19, wherein images are calculated in rapid succession to provide a time-varying three-dimensional record.

* * * * *